(12) United States Patent
Yuan

(10) Patent No.: US 8,241,492 B1
(45) Date of Patent: Aug. 14, 2012

(54) SIMULATED MOVING BED CHROMATOGRAPHY DEVICE

(76) Inventor: Leon Yuan, Taipei (TW)

( * ) Notice: Subject to any disclaimer, the term of this patent is extended or adjusted under 35 U.S.C. 154(b) by 0 days.

(21) Appl. No.: 13/330,716

(22) Filed: Dec. 20, 2011

Related U.S. Application Data

(60) Provisional application No. 61/464,874, filed on Mar. 11, 2011.

(51) Int. Cl.
 *B01D 15/08* (2006.01)
(52) U.S. Cl. ............... 210/198.2; 210/657; 210/659
(58) Field of Classification Search ............ 210/635, 210/656, 657, 659, 662, 198.2
 See application file for complete search history.

(56) References Cited

U.S. PATENT DOCUMENTS

| | | | | |
|---|---|---|---|---|
| 5,024,749 A | * | 6/1991 | Snyder et al. ............ | 204/647 |
| 7,314,551 B2 | * | 1/2008 | Frey et al. ............ | 210/198.2 |
| 7,569,141 B2 | * | 8/2009 | Hotier et al. ............ | 210/198.2 |
| 7,582,208 B2 | * | 9/2009 | Hotier et al. ............ | 210/198.2 |
| 8,182,772 B2 | * | 5/2012 | Yuan ............ | 422/637 |
| 2008/0053901 A1 | * | 3/2008 | Mierendorf et al. ...... | 210/635 |
| 2010/0329949 A1 | * | 12/2010 | Yuan ............ | 422/236 |

* cited by examiner

*Primary Examiner* — Ernest G Therkorn

(57) ABSTRACT

Disclosed herein is a simulated moving bed chromatography device comprises a minimum of one stationary pipe with a plurality of inlet/outlet channels, a rotary device next to the stationary pipes, a stationary radial flow segmented vessel communicates with the rotary device, a fluid moving device and a drive means to rotate the rotary device. The counter movement of the stationary phase and the fluid is simulated by rotating the rotary device in the same direction as the circulating fluid flow, and the fluid flows through the flow distribution segments, the stationary phase segments, the outer fluid transfer segments, holes or by passes of the improved partition plates in the flow distribution segments/compartments and outer fluid transfer segments.

20 Claims, 10 Drawing Sheets

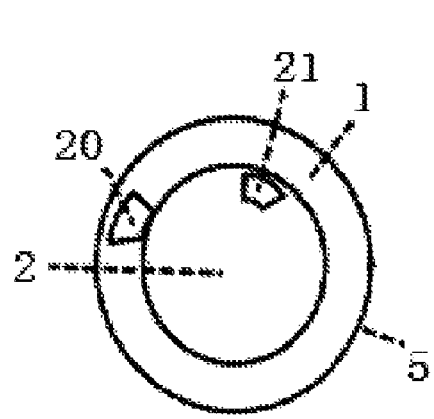
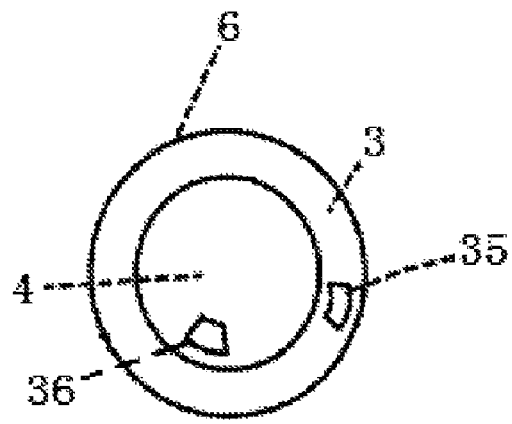
FIG. 4a FIG. 4b
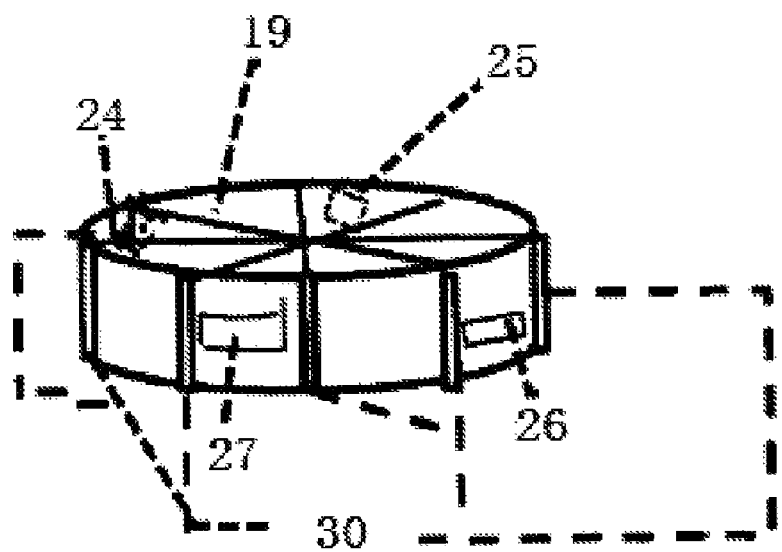
FIG. 4c

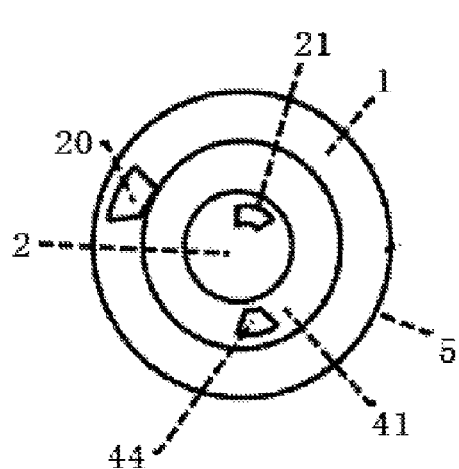
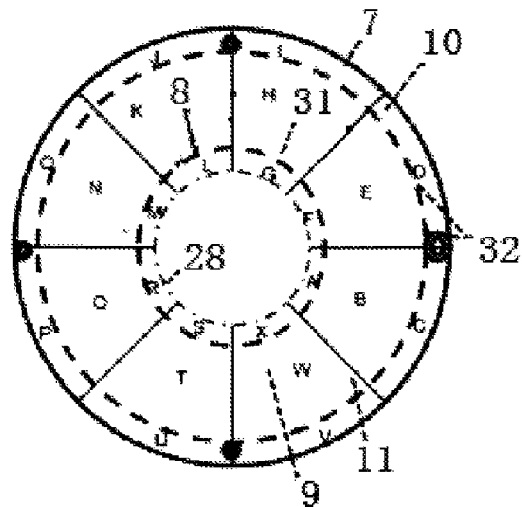
FIG. 9a
FIG. 9b
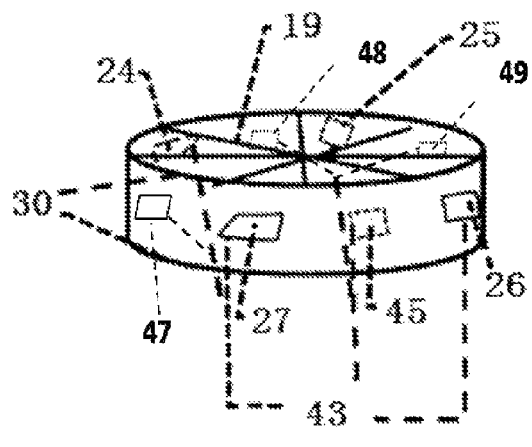
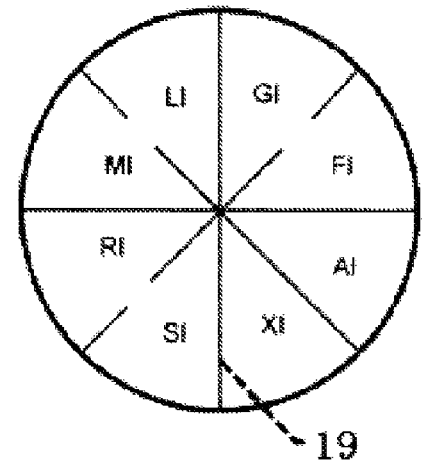
FIG. 9c
FIG. 9d

SIMULATED MOVING BED CHROMATOGRAPHY DEVICE

BACKGROUND OF THE INVENTION

1. Field of the Invention

The present invention is in the technical field of component separation. More specifically, the present invention is in the technical field of chromatography separation using a simulated moving bed of stationary phase where the fluid in the stationary phase flows in the radial direction.

2. Description of the Prior Art

Conventional chromatography separates molecules by passing sample vertically down an axial column in the batch mode. A continuous chromatography system that has high throughput and requires less solvent was described by Broughton et al in U.S. Pat. No. 2,985,589 with a simulated moving bed (SMB). The adsorption and desorption continuously take place which allows both continuous production of an extract, a raffinate stream, injection of the feed and desorbent streams. The upward movement of the adsorbent is simulated by progressive movement of the feed, desorbent, extract and raffinate access points down an adsorbent chamber. The liquid movement in the adsorbent chamber is provided by a circulation pump. Access points on the adsorbent chamber divide the chamber into separate zones. Each zone can have multiple adsorbent beds and the liquid in the cylindrical adsorbent bed moves in the axial direction.

In order to minimize the flow rate variation and channeling in the short adsorbent bed, a fluid distribution device is provided at each access point on the adsorbent chamber. A wide variety of means to introduce and withdraw fluid stream from the chamber can be used and found in U.S. Pat. Nos. 3,214,247, 3,789,989, 4,378,292, 6,024,871 and 7,314,552 B2. The fluid distribution device combines mixing, flow distribution and collecting functions. It needs to prevent backmixing and has a low dead volume and a low pressure drop. As many adsorbent beds are needed for the component separation, many fluid distributors are required.

The adsorbent chamber is packed with separation material in each bed. When a larger scale separation is required, the volume required for separation material and process flow rate are increased to meet the production rate requirement. The combination of the increase of flow rate, larger bed height and compression stress in the packing material bed leads to a high pressure drop across the packing bed. Rigid packing or large size packing material in the bed can reduce the pressure drop but results in inferior process performance.

The progressive movement of the feed, desorbent, extract and raffinate to the adsorbent chamber access points in cyclic manner is accomplished by utilizing a manifold system in which the valves in the manifold are sequentially operated. Alternately, a rotating disc valve with input and output streams connected to the access points of the adsorbent chamber can be found in prior art to replace the aforementioned valved manifold system. U.S. Pat. No. 3,040,777 to Carson et al and 3,422,848 to Liebman are the two early examples. Significant efforts have been made to the design of the rotary valve as in U.S. Pat. Nos. 4,935,464, 5,268,021, 5,366,541, 5,779,771, 5,820,656, 6,457,485, 7,544,293. The rotary valve still requires many inlet/outlet lines to communicate input and outputs streams to the access points of the adsorbent bed on the vessel.

The United States Patent Application Publication No. US 2010/0329949 A1 shows a radial flow continuous reaction/regeneration apparatus. This apparatus uses a rotary device to distribute the process feed and regeneration fluid annularly into a stationary segmented reaction/regeneration box and receiving effluents individually and annularly from the same stationary reaction/regeneration box. The flow in the segmented box is in radial direction. The radial flow continuous reaction/regeneration apparatus can be operated continuously and efficiently without the need for shutting down for regeneration. Although this device neither needs the valved manifold system nor a rotating disc valve with many input/output lines, the filler in the annular fan segment cannot move with or against the flowing fluid in the segment. It cannot be used as moving bed and the simulated moving bed has known advantages and higher efficiency over the batch system with continuous swing bed operation.

It is therefore the object of this invention to provide a Simulated Moving Bed Chromatography device to perform the continuous unattended separation of components with consistent product quality as the conventional SMB system without the need for adding more fluid distributor/collector when the number of physical separation stage increases. The new device with a mobile phase moving in radial direction combines the advantages for radial flow and rotary valve without the need to rotate the annular packed stationary phase bed. The short radial flow bed reduces the bed stress developed due to the axial flow compression and decreases pressure drop and in turn allow greater throughput and the use of more efficient soft stationary phase packing. Instead of increasing the bed height and diameter in the axial flow column, the radial flow device can increase the module height and gives higher capacity. The scaling up process is thus simpler. In order to improve the separation efficiency of the radial flow continuous reaction/regeneration apparatus described in US 2010/0329949 A1, a fluid moving device is added and the partition plate in various segments are improved with added channels or added by passes to connect adjacent segments. The stationary and fluid phases can therefore move relative to each other. The continuous reaction/regeneration apparatus or a continuous chromatography system can thus turn into a simulated moving bed chromatography device and the desorbent uses and the adsorbent loading can be reduced.

SUMMARY OF THE INVENTION

The device comprises a minimum of one stationary inlet and outlet pipe, rotational flow distribution channels, a fluid moving device, stationary segmented vessel with separated flow distribution and separated fluid transfer segments and separated stationary phase segments. Furthermore, the rotational flow distribution channels are in the rotary device that comprises rotating flow channels and face plate openings with or without a rotational flow distribution box. The rotational flow distribution channels of the rotary device receive the feed and eluent from the stationary inlet pipes and distribute the feed/eluent through the end openings of the channels into the separated flow distribution segments respectively. The flow distribution segments direct the feed and eluent to the corresponding stationary phase segments subsequently. The effluent from the stationary phase segment is fed into the outer fluid transfer segment. A fluid moving device connected to the outer fluid transfer segments is used to circulate the fluid. An alternate design has the fluid moving device connected to the stationary concentric inlet/outlet pipes and the recirculation fluid is going into and out of the device similar as the process fluids and product effluents do. The openings on the partitioning plates separating the flow distribution segments, the openings on the partition plate of the flow distribution compartment of the rotational flow distribution box and the openings on the partitioning plates separating the outer fluid transfer segments are arranged such that the fluid is recirculating in the device by the fluid moving device. The fluid in the recirculation loop circulates from a group of segments comprising a flow distribution segment, a stationary phase segment and an outer fluid transfer segment to the adjacent group of outer fluid transfer segment, stationary phase segment and flow distribution segment before going into the next group of the flow distribution, stationary phase and outer fluid transfer segments and continues on. The extract and raffinate products are the effluent streams and contain the higher concentration of desirable components and the undesirable components respectively. Each product is withdrawn from the respective stationary phase segment through the corresponding flow distribution segment into the rotational flow distribution channel of the rotary device and exits the system through the stationary concentric outlet pipe. With the multiple flow channels in the stationary pipe and in the rotary device, the feed, eluent can flow into and the products flow out of the respective stationary phase segments simultaneously according to the components concentration profile in the stationary phase segments. The simulated movement of the stationary phase is accomplished by rotating the rotary device though 360 degrees in equal angular steps and stepping through one or a set of stationary phase segments at a time. The feed and eluent in each rotating flow channel can be directed toward and the products withdrawn from each stationary phase segment in sequence according to the rotational flow distribution channel end opening position.

The fluid in each stationary phase segment flows in the radial direction in comparison to the axial direction in the conventional SMB system. The process fluid and product effluents are fed and withdrawn at the inner screen of the stationary bed and give a better even feed loading and product withdrawal than if at the outer screen with larger area. The graduate expanded packed bed distributes and collects the fluid evenly, and the conventional fluid collector, distributor and support grid for each bed is not needed with the radial flow system. The short radial flow bed has a low pressure drop with reduce axial stress which can lead to the higher throughput. Because it is possible to use higher efficiency soft media for packing and it is easy to increase physical separations stages, the efficiency of the separation is improved.

BRIEF DESCRIPTION OF THE DRAWINGS

FIG. 4a is a top view of the first rotating face plate with a set of opening according to the first embodiment of this invention;

FIG. 4b is a top view of the second rotating face plate with a second set of opening according to the first and third embodiment of this invention;

FIG. 4c is a side view of the rotational flow distribution box of a rotary device according to the first embodiment of this invention;

FIG. 9a is a top view of a rotating face plate with a set of opening according to the third embodiment of this invention;

FIG. 9b is the top view of the flow distribution, stationary phase and outer fluid transfer segments for the third embodiment of this invention that the fluid moving device is connected to the stationary inlet/outlet pipe;

FIG. 9c is a side view of the rotational flow distribution box of a rotary device for the third embodiment of this invention;

FIG. 9d is the top view of a rotational flow distribution box of a rotary device for the third embodiment of this invention.

DETAILED DESCRIPTION OF THE INVENTION

Figure 1:
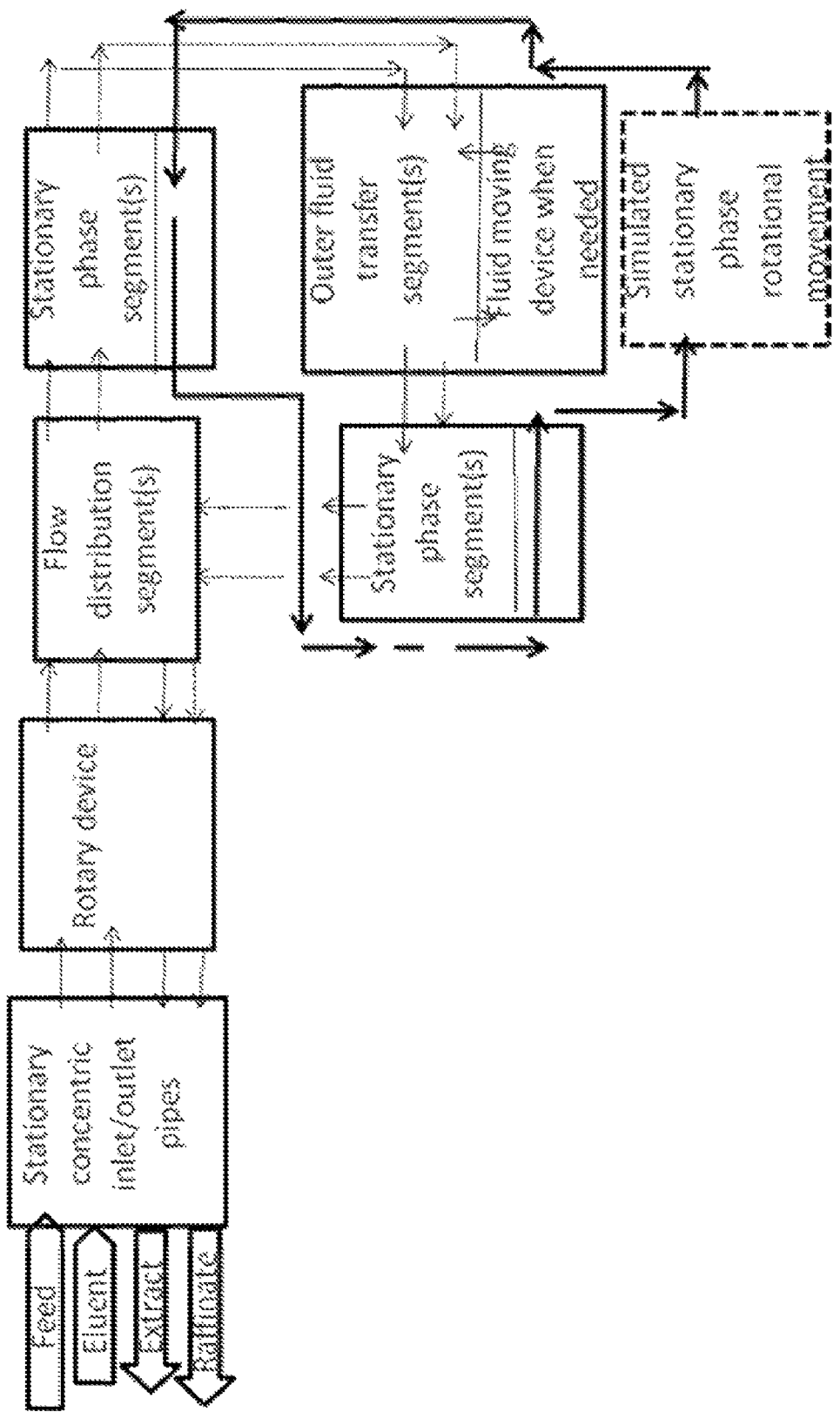
FIG. 1 is a block flow diagram for a Simulated Moving Bed Chromatography Device of this invention.

The first embodiment according to this application discloses a Simulated Moving Bed Chromatography (SMBC) Device with fluid flowing in the radial direction in each of the stationary phase segment. A block flow diagram is given in FIG. 1. This apparatus comprises a minimum of one stationary pipe with a plurality of inlet/outlet channels, a rotary device next to the stationary pipe(s), a stationary segmented vessel communicates with the rotary device and a fluid moving device to circulate the fluid in the stationary segmented vessel. The mentioned rotary device comprises a plurality of rotational flow distribution channels wherein the mentioned rotational flow distribution channels are individually employed to receive/transfer fluid from/to the inlet/outlet channels of the stationary pipe(s). Furthermore, the rotational flow distribution channels of the rotary device comprise of the rotating flow channels and face plate openings to deliver and receive the fluid through sets of face plate into and from a rotational flow distribution box of the rotary device.

The stationary segmented vessel of the first embodiment comprises a plurality of flow distribution segments, a plurality of stationary phase segments, and a plurality of outer fluid transfer segments. The flow distribution segments communicate with the rotating flow channels of the rotary device through the rotational flow distribution box. Each of the flow distribution segments is isolated from each other by the first partition plate. Every other first partition plate that separates the flow distribution segments has a second circulation mechanism which allows the two adjacent flow distribution segments to communicate to each other. The second circulation mechanism refers to: the second passage channels of the first partition plates in the stationary flow distribution segments and the second passage channels is:

a plurality of openings or channels on the first partition plate within the stationary flow distribution segments; or a plurality of bypass channels for the first partition plate of the stationary flow distribution segments and the bypass channels for the first partition plate of the stationary flow distribution segments is the piping or tubing connecting the two adjacent stationary flow distribution segments; or a flow channel formed by the removal of the first partition plate between the two adjacent stationary flow distribution segments.

Each flow distribution segment can only communicate with one of the two adjacent flow distribution segment directly though the second circulation mechanism. Each of the rotational flow distribution channels of the rotary device communicates with the corresponding flow distribution segment and each flow distribution segment communicates only to one of the rotational flow distribution channels. The stationary phase segments are outside to the flow distribution segments. Each of the stationary phase segments is isolated from adjacent stationary phase segments by the first partition plate and communicates with the corresponding flow distribution segment. The outer fluid transfer segments are outside to the stationary phase segments. Each outer fluid transfer segment communicates with the corresponding stationary phase segment and is separated from adjacent outer fluid transfer segments by the first partition plates. For each group of the two adjacent outer fluid transfer segments that are isolated from each other by the first partition plate, this segment group communicates directly to the adjacent outer fluid transfer segment group by a first circulation mechanism. The first circulation mechanism refers to: the first passage channels of the first partition plates in the outer fluid transfer segments and the first passage channel is:

a plurality of openings or channels on the first partition plate within the outer fluid transfer segments, or a plurality of bypass channels for the first partition plate of the outer fluid transfer segments and the said bypass channels is the piping/tubing connected to the two adjacent outer fluid transfer segments or is the pipe/tubing system with or without a fluid moving device connected to a set of nozzle located on the two side of the first partition plate on the outer wall of the outer fluid transfer segments, or a flow channel formed by the removal of the first partition plate between the two adjacent outer fluid transfer segments.

This radial flow simulated moving bed chromatography device further comprises a drive means to drive the rotary device to rotate according to a preset time schedule. After rotating the rotary device for a set angle, each of the rotational flow distribution channels of the rotary device is orientated to the next flow distribution segment of the stationary segmented vessel.

In one preferred example of the first embodiment, the stationary inlet/outlet pipe comprises a plurality of concentric inlet/outlet channels.

In another preferred example of the first embodiment, the stationary inlet/outlet pipe comprises a plurality of non-concentric inlet/outlet channels. Preferably, after rotating the rotary device for a set angle, the non-concentric inlet/outlet channels are positioned according to the rotational flow distribution channels of the rotary device so that each of the inlet/outlet channels can communicate with the corresponding flow distribution segment in the stationary segmented vessel through respective rotational flow distribution channel.

In one preferred example of the first embodiment, the mentioned stationary segmented vessel can further comprise a plurality of inner porous elements and a plurality of outer porous elements. Each of the inner porous elements is positioned between the flow distribution segment and the corresponding stationary phase segment. Each of the outer porous elements is positioned between the stationary phase segment and the corresponding outer fluid transfer segment. To properly distribute the fluid into the stationary phase segment, the opening on the porous elements are preferably angularly distributed evenly. The mentioned inner porous elements and the outer porous elements are individually selected from the group of: screen, perforated plate.

In one preferred example of the first embodiment, the rotary device passes through the core of the stationary segmented vessel. The rotating flow channels of the rotary device are concentric pipe channels or two set of concentric flow channels. An example set of opening at the upper face plate at the top concentric pipe channels is shown in FIG. 4a and an example set of openings at the lower face plate at the bottom concentric pipe channels is shown in FIG. 4b. The face plate openings direct fluids in the rotating flow channels flow to/from an angularly equally divided rotational flow distribution box as shown in FIG. 4c. The rotational flow distribution box is angularly equally divided by the second partition plate in this example. However, in the case that the number of equally divided compartment is greater than 8, any two adjacent compartments with no flow going though can be combined into a larger compartment.

In another preferred example of the first embodiment, the rotating flow channels of the rotary device are non concentric flow channels. Preferably, after the rotary device rotates a set angle, the openings at one end of the non-concentric rotating flow channel are positioned according to the corresponding inlet/outlet channels of the stationary pipe. The face plate openings in FIG. 4a and FIG. 4b at the other end of the non-concentric flow channels are positioned to direct the flow to the angularly equally divided rotational flow distribution box as shown in FIG. 4c. Each of the inlet/outlet channels communicates with the corresponding flow distribution segments of the stationary segmented vessel through the respective rotating flow channel and rotational flow distribution box compartment of the rotary device.

Figure 2:
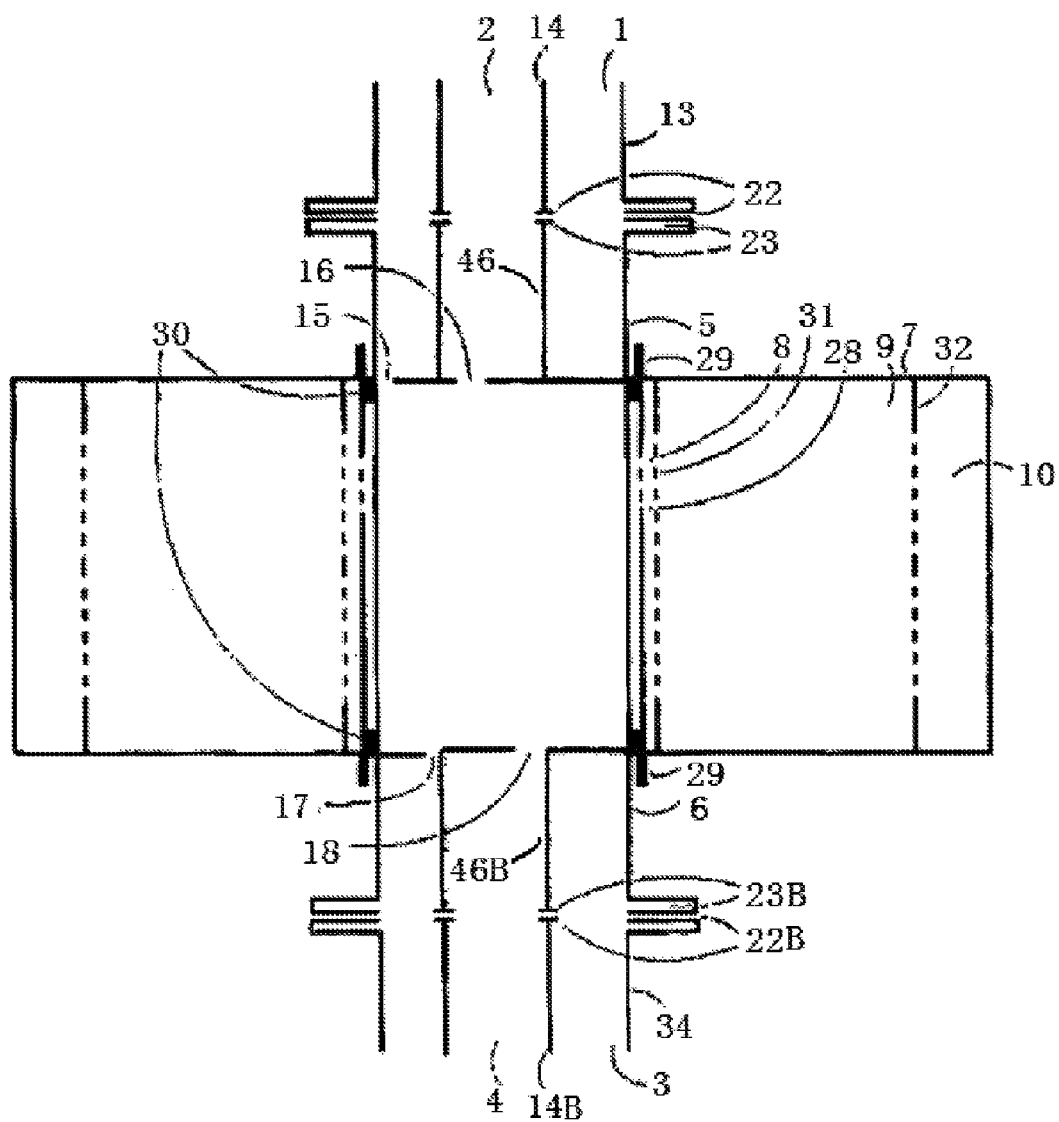
FIG. 2 is a side view of a Simulated Moving Bed Chromatography Device according to the first embodiment of this invention.
Figure 3:
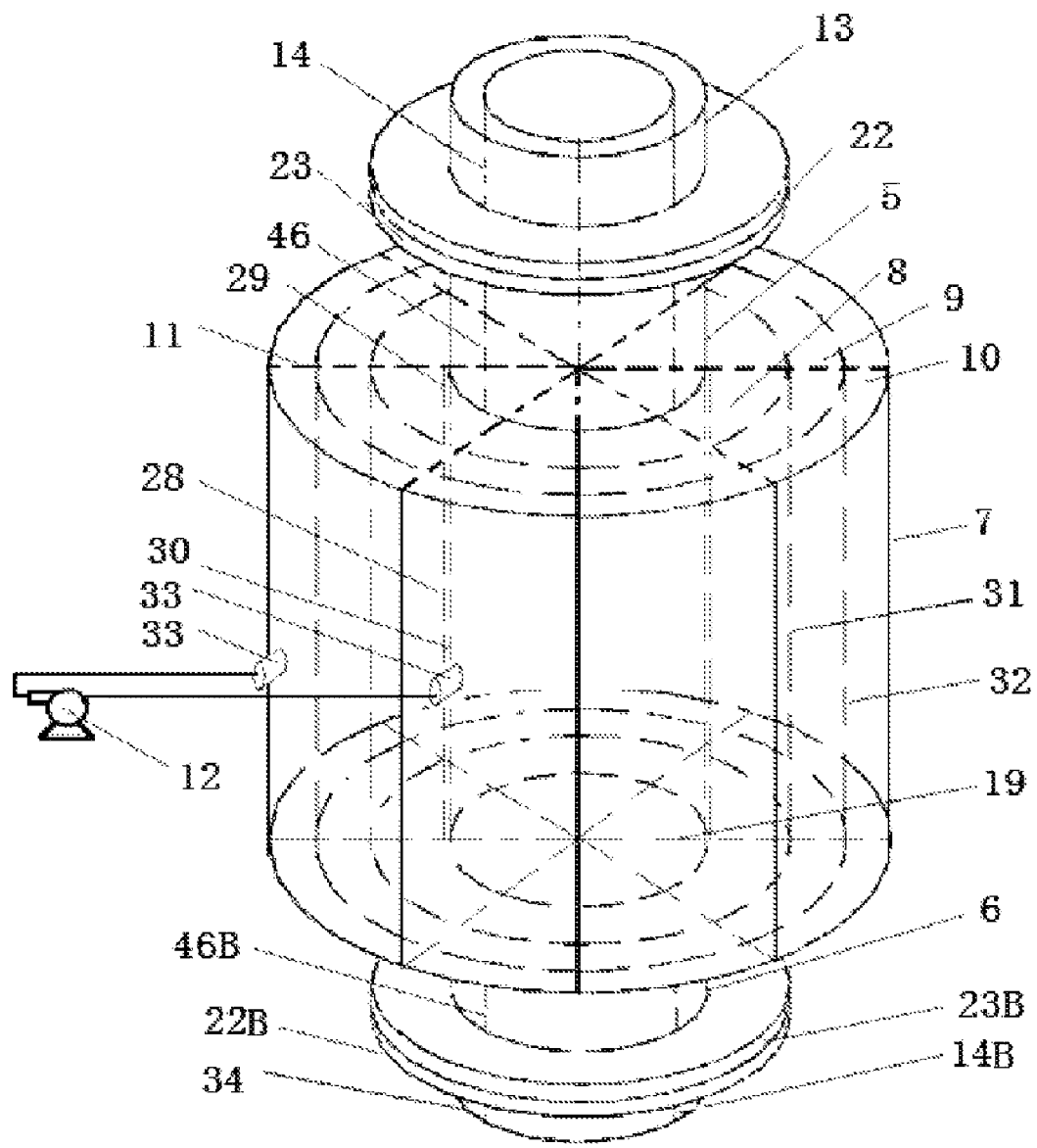
FIG. 3 is a 3D plot of a Simulated Moving Bed Chromatography Device according to the first embodiment of this invention.

FIG. 2 illustrates the side view of a simulated moving bed chromatography device two stationary pipes according to the first embodiment. FIG. 3 is a 3D plot. The numerals 1 and 2 denote the first inlet/outlet channels of the first stationary pipe 13. The fluids are separated by the concentric inner wall 14. The first stationary pipe 13 is connected to the rotary device between the top seal ring 22 and bottom seal ring 22B. The numerals 3 and 4 denote the second inlet/outlet channels of the second stationary pipe 34. The fluids are separated by the concentric inner wall 14B. The second stationary pipe 34 is also connected to the rotary device. The first portion (shown as upper portion) rotary device comprises a concentric pipe first rotational flow distribution channel 5 with rotating flow channels and face plate openings in FIG. 4a. The second portion (shown as lower portion) rotary device comprises another concentric pipe second rotational flow distribution channel 6 with rotating flow channels and face plate openings in FIG. 4b. A rotational flow distribution box is in the center core of the stationary segmented vessel 7 and is shown in FIG. 4c. The inner wall 46 separates the fluids in the first rotational flow distribution channel 5 and the inner wall 46B separates the fluids in the second rotational flow distribution channel 6. The first, second rotational flow distribution channels and the rotational flow distribution box of the rotary device are driven by a drive means, not shown in the figures, rotating about the common center of the first and second stationary pipes 13 and 34. The openings 20 and 21 at the face plate in FIG. 4a for the first and second rotating flow channels 15 and 16 above the rotational flow distribution box communicate with the first stationary pipe 13 to receive/deliver the fluid from/to the first inlet/outlet channels 1 and 2 via the annular rings formed by the concentric seal rings 22 and 23. The seal rings 22 and 23 form a fluid tight seal between fluids in the first inlet/outlet channels 1,2 and outside environment. The openings 35 and 36 at the face plate in FIG. 4b for the third and fourth rotating flow channels 17 and 18 below the rotational flow distribution box communicate with the second stationary pipe 34 to receive/deliver the fluid from/to the first inlet/outlet channels 3 and 4 via the annular rings formed by the concentric seal rings 22B and 23B. The seal rings 22 and 23, 22B and 23B form fluid tight seal between fluids in the channels 1,2,3,4 and outside environment. The rotational flow distribution box of the rotary device is extending into the center hole of the stationary segmented vessel 7 through the seal ring element 29. The tight clearance between the seal ring element 29 and the rotary device with the rotational flow distribution channels 5 and 6 prevent excessive fluid communication between the outside environment and the internals of the stationary segmented vessel 7.

Figure 5:
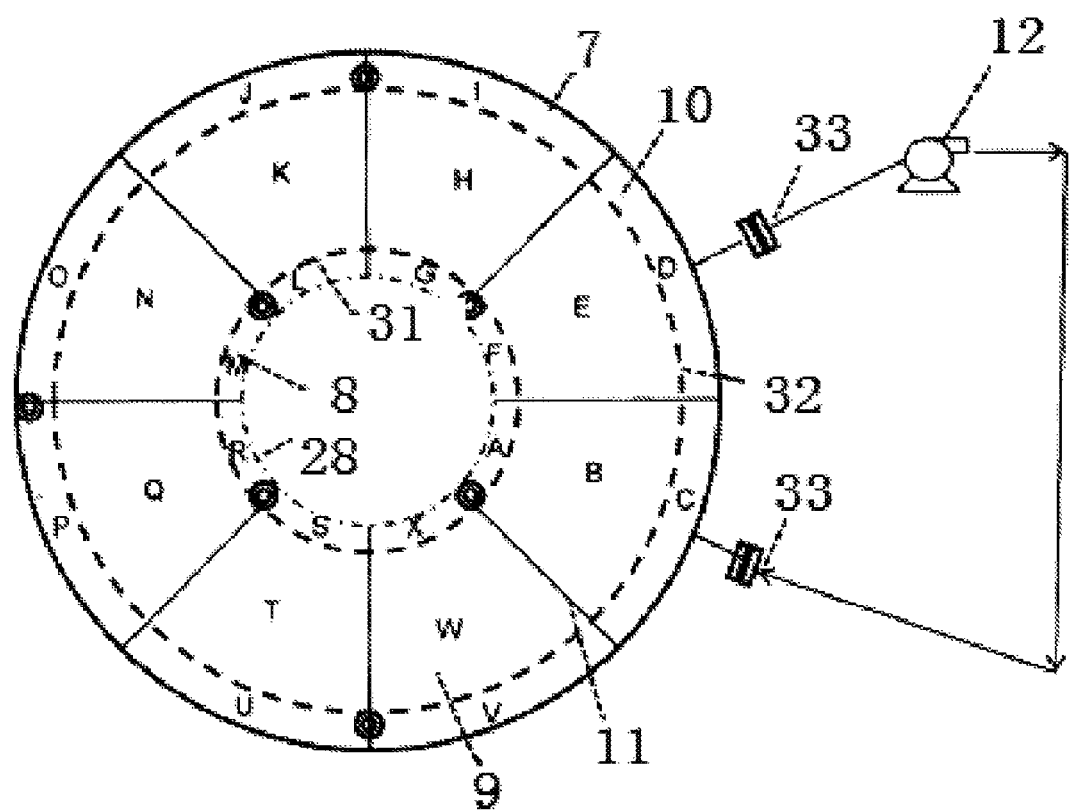
FIG. 5 is the top view of the flow distribution, stationary phase and outer fluid transfer segments with a fluid moving device according to the first embodiment of this invention.

The rotational flow distribution box for the first embodiment of the simulated moving bed chromatography device is angularly divided into 8 equal compartments by partition plates 24 in FIG. 4c. The solid plates 24 prevent the cross contamination between different fluids in the rotational flow distribution box compartments and direct the fluid to the proper locations. The number of compartments is typically equal to the number of time steps of a process cycle. In this illustration, one process cycle with a full 360 degree rotation is divided into 8 time steps and there are 8 compartments in the rotational flow distribution box. The number of time steps is also equal to the number of stationary phase segments 9 as shown in FIG. 5. The feed from the first inlet channel 1 at the outer annular position of the first stationary pipe 13 flows into the rotational flow distribution channel 5 and the first rotating flow channel the respective compartment of the rotational flow distribution box in FIG. 4c. The effluent (raffinate) from the corresponding flow distribution compartment in the rotational flow distribution box of the rotary device in FIG. 4c flows though the second rotating flow channel 16 end face plate opening(s) before flows into the first outlet channel 2 at the center of the first stationary pipe 13. The peripheral of the rotational flow distribution box of the rotary device has openings align with the openings of corresponding stationary flow distribution segments 8 in FIG. 2 and FIG. 5. The clearance between the seal elements 30 and innermost perforated plate/screen wall 28 are kept at minimum for smooth rotation and minimum cross leakages. Eight straight and two circular (top and bottom) sealing elements 30 on the rotational flow distribution box of the rotary device are shown in FIG. 4c to prevent cross leakages between fluids in the rotary device. To minimize the contamination of the extract product, it is preferable to keep the rotating flow channels where feed enters and raffinate exits away from the rotating flow channel through which the extract exits. The first embodiment illustrates that the feed enters and raffinate exits through the top rotating flow channels whereas the eluent enters and extract exits through the bottom rotating flow channels.

FIG. 5 gives the top view of the flow distribution segments, the stationary phase segments and the outer fluid transfer segments. Porous elements (concentric perforated plates, sintered metals or screens) are used to separate the stationary phase segments from the flow distribution and outer fluid transfer segments. The segments in each of the flow distribution, outer fluid transfer and stationary phase segment group are in annular fan shape and are separated from each other by the first partition plates 11. Every segment in the stationary phase segments is loaded with stationary phase filler, and the filler is confined by the inner and outer porous elements 31, 32 and first partition plates 11. The flow distribution segments 8 are segmented and bounded by the first partition plate 11 and innermost plate/screen 28 and inner porous element 31. The outer fluid transfer segments 10 are bounded by the first partition plate 11, inner wall of the stationary segmented vessel 7 and outer porous element 32. The numbers of the flow distribution segments, the outer fluid transfer segments and the stationary phase segments are the same. The innermost plate/screen 28, as shown in FIG. 2 and FIG. 5, has openings to the flow distribution segments 8 which align with the openings of the rotating flow channels 15,16,17 and 18 in FIG. 2, face plate openings 20,21,35 and 36 in FIGS. 4a and 4b, and openings 24,25,26 and 27 at the circumference of the rotational flow distribution box in FIG. 4c. As openings of the rotating flow channels 15, 16, 17 and 18 and opening 20,21,35 and 36 on the face plates of the rotary device, as shown in FIGS. 4a, 4b and 4c, rotate stepwise through 360 degree cycle, openings on innermost plate/screen 28 communicate the rotating flow channels 15, 16, 17 and 18 with the stationary flow distribution segments 8 respectively. The first inlet channel 1 with feed communicates with the stationary phase segments through rotating flow channel 15 and respective flow distribution segment 8, the second inlet channel 3 with eluent communicates with the stationary phase segments through rotating flow channel 17 and corresponding flow distribution segment 8, the first outlet channel 2 with raffinate communicates with the stationary phase segments through rotating flow channel 16 and corresponding flow distribution segment 8 and the second outlet channel 4 with extract communicates with the stationary phase segments through rotating flow channel 18 and corresponding flow distribution segment 8 simultaneously at a given time step. Each stationary phase segment communicates with the fluid in the inlet/outlet channel for ⅛ of the cycle as the process steps through 360 degrees sequentially. To keep the recirculation fluid movement in the stationary phase, a fluid moving device 12 to circulate the fluid is connected to nozzles (33) located at the outer wall of two adjacent outer fluid transfer segments. The process fluid is circulating in clockwise direction as shown in FIG. 5. To simulate the movement of the stationary phase filler, the rotary device rotates in the pump around fluid flow direction to simulate the counter current movement of the stationary phase to the pump around fluid flow. When the stationary phase filler has the capability to differentially retard the movement of the feed components in the fluid flow, the device behaves as a chromatography separation device.

The pump around fluid circulating device 12 circulates fluid flow inside the stationary segmented vessel in the first embodiment of the simulated moving bed chromatography device. The circulating fluid moves from the segment D though nozzle 33, fluid circulating device 12 to the second nozzle 33 before enters the segment C in FIG. 5. The circulating fluid continues flow radially inward through the stationary phase in the segment B to the flow distribution segments A. The circulating fluid flow continues through the openings on the first partition plate 11 into the flow distribution segment X and radially outward through the stationary phase in the segment W before reaching the outer fluid transfer segment V. The circulating fluid flow continues through the openings on the first partition plate 11 into the outer fluid transfer segment U and continues flowing through each individual segment T,S,R,Q,P,O,N,M,L,K,J, I,H,G,F,E and D to complete the fluid circulation loop. The rotary device is rotating stepwise at one segment each time (45 degrees per segment) in the same direction as the circulating fluid flow. For a given step, the feed is added to the flow distribution segment M in where the circulating fluid inside the segment has mixed component concentration. The eluent is added to the flow distribution segment A in where the circulating fluid has the relatively similar component concentration to the eluent. The extract is withdrawn from the flow distribution segment S in where the circulating fluid has equal or higher concentration or purity of the flow retarded component than that inside of the segment R or X. The raffinate is withdrawn from the flow distribution segment G in where the fluid has equal or higher concentration or purity of the less flow retarded component than that inside of the segment F or L. As the fluid is circulated by the device 12 and the concentration profile moves in the clockwise direction, the rotary device rotates in the same clockwise direction to inject the feed and eluent and to withdraw the extract and raffinate in synchronization with the component concentration profile movement in the stationary phase segmented vessel.

Figure 6:
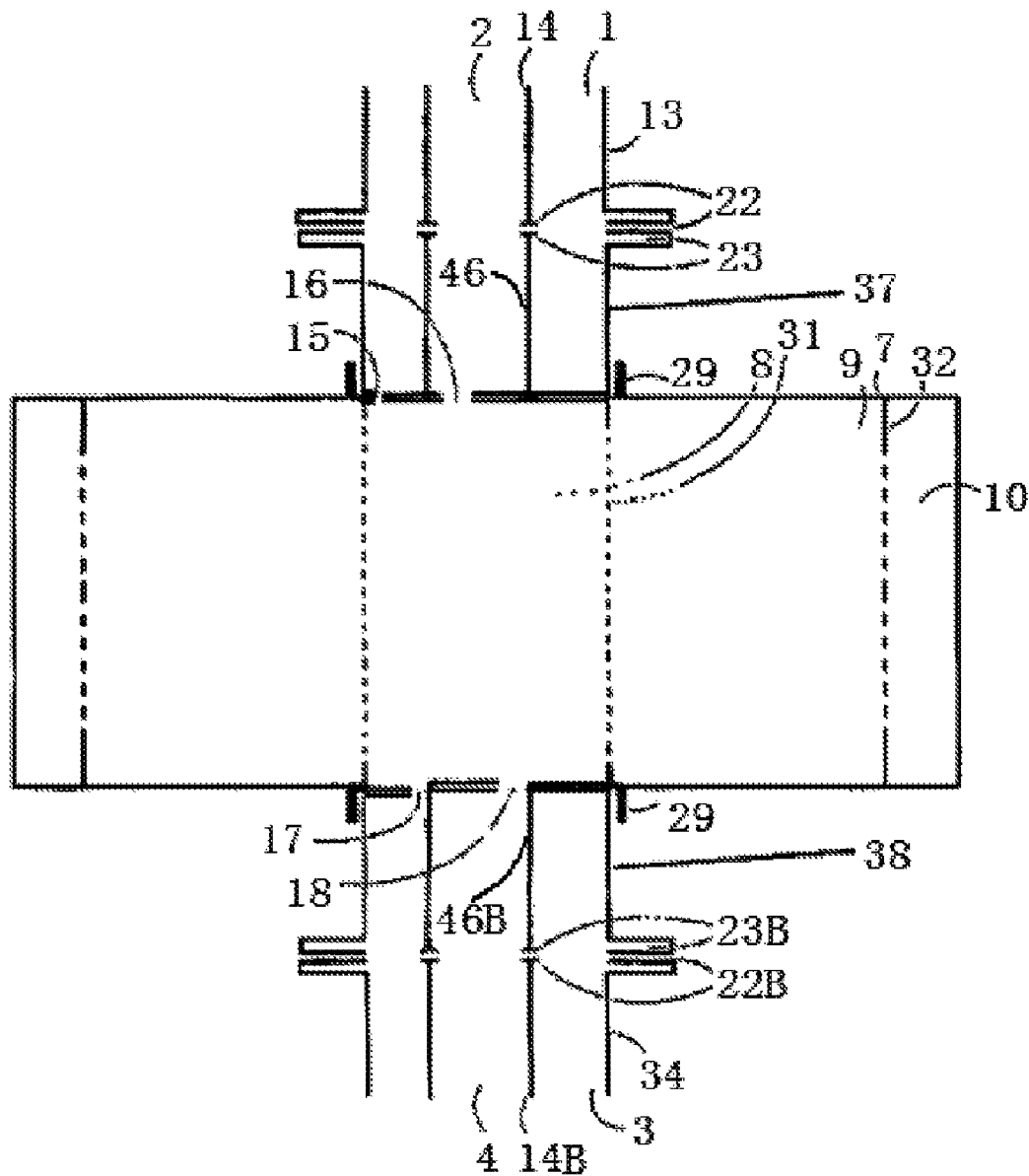
FIG. 6 is a side view of a Simulated Moving Bed Chromatography Device according to the second embodiment of this invention.

The second embodiment of this application is different from the first embodiment in that the rotary device has no rotational flow distribution box and comprises a first rotary part and a second rotary part, wherein the first rotary part is between the first stationary pipe and the stationary segmented vessel, and the second rotary part is between the stationary segmented vessel and the second stationary pipe as shown in FIG. 6. The second embodiment of this application comprises first and second stationary pipes 13 and 34 with inlet/outlet channels 1,3,2 and 4, a rotary device with the first and second parts next to the stationary pipes, a stationary segmented vessel 7 communicates with the rotary device. The mentioned rotary device comprises the third and the fourth rotational flow distribution channels 37 and 38 wherein the mentioned rotational flow distribution channels are individually employed to receive/transfer fluid from/to the inlet/outlet channels of the stationary pipes. Furthermore, the rotational flow distribution channels of the rotary device comprise of the rotating flow channels 15,16,17 and 18 and face plate openings to deliver/receive the fluid to/from the flow distribution segments of the stationary segmented vessel.

Figure 7A:
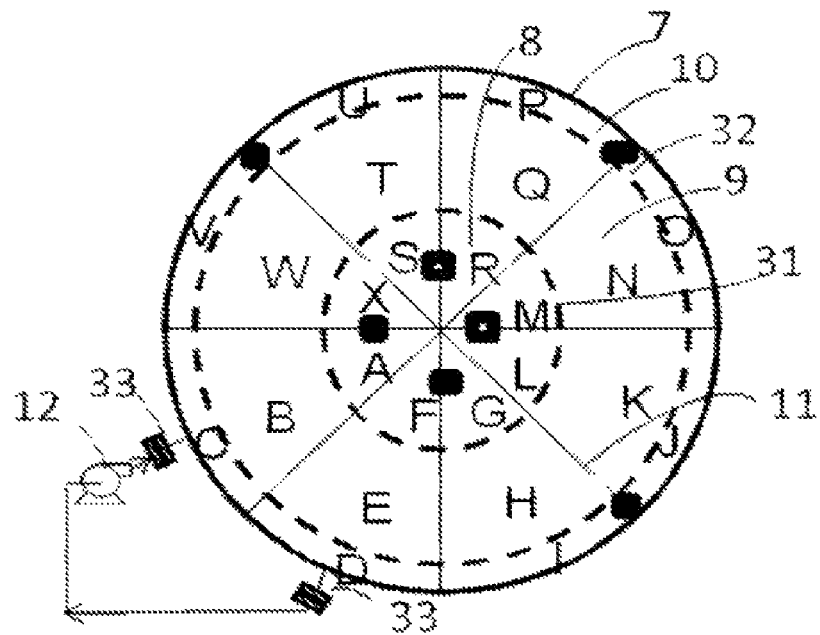
FIG. 7a is the top view of the flow distribution, stationary phase and outer fluid transfer segments with a fluid moving device according to the second embodiment of this invention.
Figure 7B:
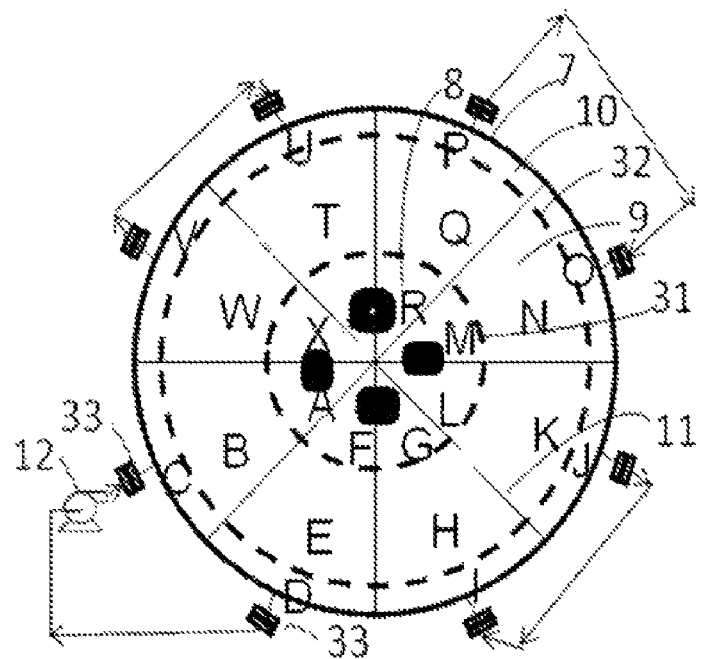
FIG. 7b is the top view of an alternate design of the flow distribution, stationary phase and outer fluid transfer segments with a fluid moving device according to the second embodiment of this invention.

The stationary segmented vessel of the second embodiment comprises a plurality of flow distribution segments 8, a plurality of stationary phase segments 9, and a plurality of outer fluid transfer segments 10. The flow distribution segments 8 communicate with the rotating flow channels of the rotary device through the face plate openings of the rotational flow distribution channels. Each of the flow distribution segments is isolated from each other by the first partition plates 11 as shown in FIG. 7*a* or 7*b*. Every other first partition plate that separates the flow distribution segments has an aforementioned second circulation mechanism which allows the two adjacent flow distribution segments to communicate to each other. A typical second circulation mechanism with openings on the first partition plate is shown as solid squares for a system with 8 flow distribution segments. Each of the rotational flow distribution channels of the rotary device communicates with the corresponding flow distribution segment and each flow distribution segment communicates only to one of the rotary device rotational flow distribution channels. The stationary phase segments 9 are outside to the flow distribution segments 8. Each of the stationary phase segments is isolated from each other by the first partition plates 11 and communicates with the corresponding flow distribution segment. The outer fluid transfer segments 10 are outside to the stationary phase segments. Each outer fluid transfer segment communicates with the corresponding stationary phase segment 9 and is separated from each other by the first partition plates 11. For each set of the two adjacent outer fluid transfer segments 10 that are isolated from each other by the first partition plates 11, it communicates to the adjacent set outer fluid transfer segments by an aforementioned first circulation mechanism and examples are given in FIG. 7*a* or 7*b* with either opening(s) on the first partition plates shown as solid squares or by connecting nozzles on the vessel wall.

In one preferred example of the second embodiment, the stationary inlet/outlet pipe comprises a plurality of concentric inlet/outlet channels.

In another preferred example of the second embodiment, the stationary inlet/outlet pipe comprises a plurality of non-concentric inlet/outlet channels. Preferably, after rotating the rotary device for a set angle, the non-concentric inlet/outlet channels are positioned according to the rotational flow distribution channels of the rotary device, so that each of the inlet/outlet channels can communicate with the corresponding flow distribution segment in the stationary segmented vessel through respective rotational flow distribution channel.

In one preferred example of the second embodiment, the mentioned stationary segmented vessel can further comprise a plurality of inner porous elements and a plurality of outer porous elements. Each of the inner porous elements is positioned between the flow distribution segment and the corresponding stationary phase segment. Each of the outer porous elements is positioned between the stationary phase segment and the corresponding outer fluid transfer segment. To properly distribute the fluid into the stationary phase segment, the opening on the porous elements are preferably evenly distributed angularly. The mentioned inner porous elements and the outer porous elements are individually selected from the group of: screen, sintered metal, perforated plate.

In one preferred example of the second embodiment, the rotating flow channels of the rotary device are concentric pipe channels or two set of concentric flow channels. An example set of opening at the upper end face plate of the concentric pipe channels is shown in FIG. 4*a* and an example set of openings at the lower end face plate of the concentric pipe channels is shown in FIG. 4*b*. The face plate openings direct fluids in the rotating flow channels flow to/from angularly equally divided flow distribution segments (A,F,G,L,M,R,S, X) in the stationary segmented box as shown in FIG. 7*a* or 7*b*.

In another preferred example of second embodiment, the rotating flow channels of the rotary device are non concentric flow channels. Preferably, after the rotary device rotates for a set angle, the openings at one end of the non-concentric rotating flow channel are positioned according to the corresponding inlet/outlet channels of the stationary pipe. The face plate openings in FIG. 4*a* and FIG. 4*b* at the other end of the non-concentric flow channels are positioned to direct the fluids flow to the angularly equally divided flow distribution segments (A,F,G,L,M,R,S,X) in FIG. 7*a* or 7*b*. Each of the inlet/outlet channels communicates with the different flow distribution segments in the stationary segmented vessel through the respective rotational flow distribution channel of the rotary device.

A typical example for a side view of the simulated moving bed chromatography device according to the second embodiment is given in FIG. 6. The top view of a stationary segmented vessel according to the second embodiment is shown in FIG. 7*a*. Another top view of an alternate design stationary segmented vessel according to the second embodiment is shown in FIG. 7*b*. The rotational flow distribution box in the first embodiment as in FIG. 4*c* is eliminated and the stationary flow distribution segment location is changed. The stationary flow distribution segments are in fan shape located at the center for the second embodiment instead of in the annular fan shape for the first embodiment. The first rotary part and the second rotary part are driven by the same driving means or two synchronized driving means rotate with a preset time schedule. The rotary device rotates 45 degree or one angular segment for each time step.

In one preferred example of the second embodiment, the first (top) and second (bottom) end face plate in FIG. 4a and FIG. 4b of the rotational flow distribution channels in FIG. 6 have polished flat surfaces with proper openings such as 20, 21, 35 and 36. The stationary concentric seal rings 22 form seals with the flat polished surface seal ring 23 to separate the fluids in the channels 1 and 2. The stationary concentric seal rings 22B form seals with the flat polished surface seal ring 23B to separate the fluids in the channels 3 and 4. The inlet channel 1 communicates with the openings of the rotational flow distribution channel 15 of the rotary device. The inlet channel 3 communicates with the openings of the rotational flow distribution channel 17 continuously as the rotary device rotates 360 degrees step by step through each time step. The fluids flow into one end of the rotational flow distribution channel openings and exit at the corresponding openings at the other end of the rotational flow distribution channels. The face plates of the third and fourth rotational flow distribution channel 37 and 38 have the flat polished surface and form seals with the top and bottom surfaces at the center section of the first partition plate 11. The fluids in the rotating flow channels 15,16,17 and 18 of the rotary device communicate with the stationary flow distribution segments 8 of FIGS. 6 and 7a through the face plate openings 20,21,35 and 36. Each of the flow distribution segments 8 is separated from each other by the first partition plate 11 and every other first partition plate 11 has channel(s) or opening(s) to communicate the two neighboring flow distribution segments directly. The openings are shown as dark solid squares in FIGS. 7a and 7b. The flow distribution segments 8 communicate with the stationary phase segments 9 through the inner porous element 31. The stationary phase segments 9 are outside to the flow distribution segments 8. Each of the stationary phase segments is isolated from each other by the first partition plate 11. The outer fluid transfer segments 10 are outside to the stationary phase segments 9. Each of the outer fluid transfer segments is isolated from each other by the first partition plate 11. Each of the outer fluid transfer segments 10 can communicate directly to only one of its neighboring outer fluid transfer fan segment through openings on the first partition plate 11 or through the nozzles on the stationary segmented vessel wall. The openings and nozzles are shown as dark solid squares in FIG. 7a and FIG. 7b.

To properly distribute the fluids into the stationary phase segment for the second embodiment, the openings on the porous elements 31 and 32 in FIGS. 6, 7a and 7b are preferably evenly distributed angularly that the flow resistance of the opening are the same.

In one preferred example of the second embodiment, the first and second rotary parts in FIG. 6 rotate in phase and are connected by a shaft (not shown) going through the center of the stationary flow distribution segments 8 and located on the opposite side of the stationary segmented vessel. The process feed enters the inlet channel 1 and the eluent enters inlet channel 3, the raffinate exits the outlet channel 2 and the extract exits the outlet channel 4. The rotating flow channels where the feed enters and raffinate exits are away from the rotating flow channel through which the extract exits to minimize the extract product contamination.

FIGS. 7a and 7b show the top view of the flow distribution segments 8, the stationary phase segments 9 and the outer fluid transfer segments 10 according to the second embodiment of this application. Porous elements (concentric perforated plates, sintered metal or screens) are used to separate the stationary phase segments 9 from the inner flow distribution segments 8 and outer fluid transfer segments 10. The flow distribution segment comprises eight fan shape segments at the center of the stationary segmented vessel 7. The outer fluid transfer segments 10 or the stationary phase segments 9 comprise of eight annular fan shape segments respectively. The segments of each group are angularly divided equally by the first partition plates 11. Each segment in the stationary phase segments 9 is loaded with stationary phase filler. The filler is confined by the porous elements 31, 32 and the first partition plates 11. The flow distribution segments 8 are segmented and bounded by the first partition plate 11 and the inner porous element 31. The outer fluid transfer segments 10 are segmented and bounded by the first partition plate 11, inner wall of the stationary segmented vessel 7 and outer porous element 32. The numbers of the flow distribution segments, the outer fluid transfer segments and the stationary phase segments are the same. The openings of the rotating flow channels 15,16,17 and 18 in FIG. 6 communicate to either the top or the bottom of the corresponding flow distribution segment 8 in FIG. 6, FIG. 7a or FIG. 7b. As the openings of the face plates 20,21,35 and 36 in FIGS. 4a and 4b rotate stepwise through 360 degree during a process cycle, the fluid is distributed to or receiving from the respective stationary flow distribution segment 8. The inlet channel 1 with feed communicates with the stationary phase segment through rotating flow channel 15 and respective flow distribution segment 8, the inlet channel 3 with eluent communicates with the stationary phase segments through rotating flow channel 17 and respective flow distribution segment 8, the outlet channel 2 with raffinate communicates with the stationary phase segments through the rotating flow channel 16 and the respective flow distribution segment 8 and the outlet channel 4 with extract communicates with the stationary phase segments through the rotating flow channel 18 and the flow distribution segments 8 simultaneously at a given time step. Each respective stationary phase segment communicates with the inlet/outlet channel for ⅛ of the cycle time as the rotary device steps through 360 degree sequentially. A fluid moving device 12 connected to nozzles 33 located at the wall of two adjacent outer annular fluid transfer segments is used to circulate the process fluid. The process fluid is circulating in the clockwise direction as shown FIGS. 7a and 7b. To simulate the counter movement of the stationary phase with the process flow, the rotary device rotates in the fluid flow direction.

The operation of the rotary device for the first and second embodiment is similar. A complete 360 degree rotation of the rotary device comprises of multiple time steps with feed, eluent and effluents that flow radially into or out of the packed annular fan shape stationary phase segments. The stationary phase between the inner and outer porous elements in the vessel is equally divided into angular segments in an annular fan shape by the first partition plates and the number of time steps is typically equal to or is ½ of the number of annular fan segment. By stepwise rotation of the rotary device to distribute the fluids into the flow distribution segments or to receive the fluid from the flow distribution segments, the feed, eluent and effluents are passed successively into or from the respective stationary phase segments. Each stationary phase segment goes through different process conditions at different time step and completes one process cycle with a full 360 degree rotation of the rotary device.

In the first and second embodiment, the mentioned filler has the property to differentially retard the movement of the feed components in the fluid flow. When the device is employed as a reactor, the feeds contain components which are capable of promoting reactions of other components in the feeds. The catalytic components flow along with the reactive components in the feed and preferably do not flow with the products from the reaction.

The movement of the fluid flow and stationary phase of the first and second embodiment is similar. The fluid flow is circulated inside the stationary segmented vessel by the fluid moving device 12. The circulating fluid according to the second embodiment flows from the segment D though nozzle 33, fluid mvoing device 12 to nozzle 33 before enters the segment C in FIG. 7a or 7b. The circulating fluid continues flows radially inward through stationary phase in the segment B to the flow distribution segments A and X and radially outward through stationary phase in the segment W before reaching the outer fluid transfer segments V and U. The circulating fluid continue flows through each individual segment T,S,R,Q,P,O,N,M,L,K,J, I,H,G,F,E and D to complete the fluid circulation loop. The rotary device rotates stepwise in one segment at each time (45 degrees per segment) in the same direction as the circulating fluid flow. For a given step, the feed is added to the flow distribution segment X where the circulating fluid inside the segment has mixed component concentration. The eluent is added to the flow distribution segment L where the circulating fluid has the relatively similar component concentration to the eluent. The extract is withdrawn from the flow distribution segment F where the circulating fluid has equal or higher concentration or purity of the flow retarded component than that inside of the segment G or A. The raffinate is withdrawn from the flow distribution segment R where the circulating fluid has equal or higher concentration or purity of the less flow retarded component than that inside of the segment S or M. As the fluid is circulated by the device 12 and the concentration profile of the circulating fluid moves in the clockwise direction, the rotary device rotates in the same clockwise direction to inject the feed and eluent and to withdraw the extract and raffinate in synchronization with the component concentration profile movement in the stationary phase segmented vessel.

Depending on the process application, the number of segments separated by the first partition plate 11 and the number of compartments separated by the partition plate 24 can increase, the feed addition and effluent withdrawal segment locations can change as required. Instead of using the second circulation mechanism on the first partition plate 11 to communicate sets of two adjacent flow distribution segments and the first circulation mechanism to communicate sets of two adjacent outer fluid transfer segments, these mechanisms can be replaced with any form of flow channels with the sole purpose of establishing fluid circulation loop inside the stationary segmented vessel. A third circulation mechanism is used to replace the second circulation mechanism according to the third embodiment of this application.

Figure 8:
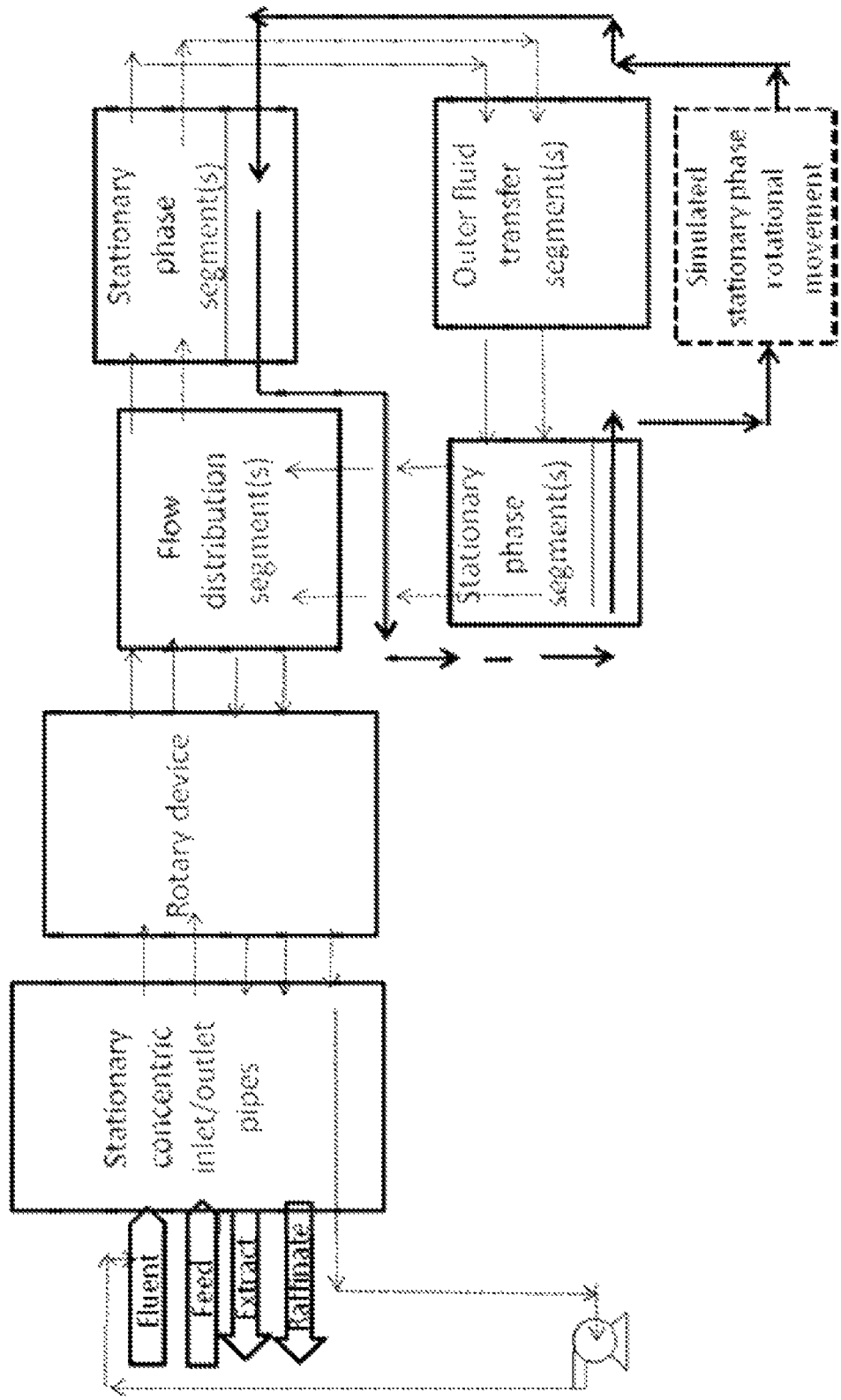
FIG. 8 is a block flow diagram for a Simulated Moving Bed Chromatography Device according to the third embodiment of this invention.

In one preferred example of the third embodiment, the fluid moving device is connected to the stationary inlet/outlet pipe in comparison to that the fluid moving device is connected to the nozzles at the outer wall of the stationary segmented vessel in the first or second embodiment. The fluid moving device is connected to the stationary inlet/outlet pipe according to the third embodiment and still meets the sole purpose of providing the recirculating fluid pressure loss in the circulation loop. A block flow diagram according to the third embodiment of this invention is shown in FIG. 8. The third circulation mechanism replaces the second circulation mechanism. The third circulation mechanism refers to: the third passage channels of the second partition plates in the rotational flow distribution box and the third passage channels is:

a plurality of openings or channels on the second partition plates within the rotational flow distribution box; or a plurality of bypass channels for the second partition plates of the rotational flow distribution box compartments and the bypass channels for the second partition plate of the rotational flow distribution box compartments is the piping or tubing connecting the two adjacent flow distribution box compartments; or a flow channel formed by the removal of the second partition plate between the two adjacent rotating flow distribution compartments; or a flow path channels through the rotational flow distribution box compartment, the rotating flow channel, stationary outlet channel, connecting pipes, stationary inlet channel, rotational flow distribution channel and the adjacent rotational flow distribution box compartment or the flow path channels through the rotational flow distribution box compartment, rotating flow channel, stationary outlet channel, fluid moving device, stationary inlet channel, rotating flow channel and the adjacent rotational flow distribution box compartment.

Figure 10:
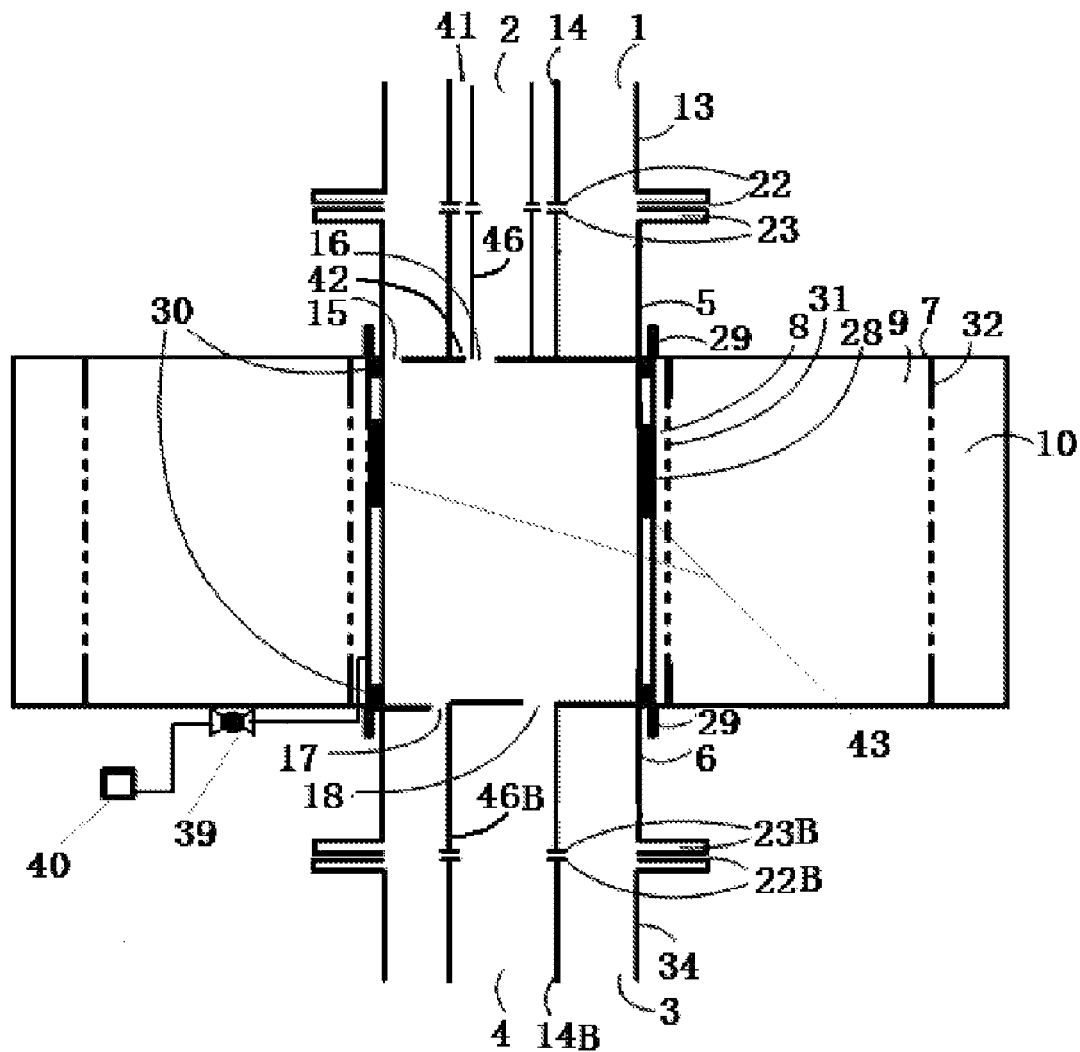
FIG. 10 is a side view of a Simulated Moving Bed Chromatography Device for the third embodiment of this invention with a cross contamination prevention/depressurization system that the fluid moving device is connected to the stationary inlet/outlet pipe.

In one preferred example of the third embodiment, the circulation fluid flows out of the system through a first flow distribution segment and rotary device into the stationary pipes and then circulated by the fluid moving device back to the rotary device and a second flow distribution segment. In order to establish fluid recirculation loop, the first partition plates 11 inside the flow distribution segments have no second circulation mechanism to communicate to the adjacent flow distribution segment as shown in FIG. 9b. Instead, the second partition plates 19 inside the rotational flow distribution box in FIG. 9c have the third circulation mechanism as shown in FIG. 9d with openings between compartments SI and RI, MI and LI, GI and FI. For every other second partition plate in the rotational flow distribution box compartments, there is one second partition plate with third passage channel. Instead of the first rotating face plate with two openings in the first embodiment, the first rotating face plate according to the third embodiment is shown in FIG. 9a with three openings. The time step for the process cycle changes from eight to four for the third embodiment. The rotary device rotates 90 degrees instead of 45 degrees for each step. The circulating fluid flows from the flow distribution segment A through the opening 26 at the peripheral of the rotational flow distribution box in FIG. 9c and into the compartment AI in FIG. 9d. It flows through the second rotating face plate opening 35 in FIG. 4b and the third rotating flow channel 17 in FIG. 10 and stationary inlet/outlet 3 and flows into the suction of the fluid moving device in FIG. 8. The fluid from the discharge of the fluid moving device joins the eluent and flows into stationary inlet pipe 41 in FIG. 10, continues flowing through the fifth rotating flow channel 42 and the first rotating face plate opening 44 in FIG. 9a and flows into flow distribution compartment XI in FIG. 9d. The circulating fluid continue moves through the rotational flow distribution box opening 45 at the peripheral in FIG. 9c and segments X,W,V,U,T,S in FIG. 9b and opening 27 in FIG. 9c, compartments SI, RI in FIG. 9d, opening 47 in FIG. 9c, segments R,Q,P,O,N,M in FIG. 9b, opening 24 in FIG. 9c, compartments MI and LI in FIG. 9d, opening 48 in FIG. 9c, segments L,K,J,I,H,G in FIG. 9b, opening 25 in FIG. 9c, compartments GI and FI in FIG. 9d, opening 49 in FIG. 9c, segments F,E,D,C,B and returns to the flow distribution segment A in FIG. 9b to complete the circulation. The flow patterns for the feed, raffinate and extract remain the same as in the first embodiment. The feed from the inlet channel 1 at the outer annular position of the first stationary pipe 13 flows into the first rotating flow channel 15, the first face plate opening 20 into the circulating fluid in the flow distribution compartment MI of the rotational flow distribution box in FIG. 9d. The effluent (raffinate) from the circulating fluid in the flow distribution compartment GI flows through the first face plate opening 21 in FIG. 9a and the respective second rotating flow channel 16 of the rotary device in FIG. 10 before flowing into the first outlet channel 2 at the center of the first stationary pipe 13. The extract from the second outlet channel 4 comes from the circulating fluid in the flow distribution compartment SI in FIG. 9d and the second face plate opening 36 in FIG. 4b and the fourth rotating flow channel 18. The seals 29 can also take different form with the sole purpose to isolate each flow channels and avoid leakages. Instead of the seals 30 shown in FIG. 4c, seals can be also set up around the openings 24,25,26,27,45,47,48, and 49 at the peripheral of the rotational flow distribution box in FIG. 9c. The leakage from the seal 43 around the openings in FIG. 9c can be vented to outside of the device by installing a depressurization and contamination prevention system located at the outside of the rotational flow distribution box. This depressurization and contamination prevention system comprises seal leakage valve 39 and seal leakage meter 40 as shown in FIG. 10. The seal leakage valve 39 has an inlet end that communicates with the space between the innermost plate 28 and rotational flow distribution box, and the seal leakage meter 40 can be situated at either side of the seal leakage valve 39. The seal leakage meter is used to detect the overall rate of seal leakage.

Although specific embodiments have been illustrated and described herein, it is obvious to those skilled in the art that many modifications of the present invention may be made without departing from what is intended to be limited solely by the claims of this application. Unless otherwise explained, all technical and scientific terms used herein have the same meaning as commonly understood by one of ordinary skill in the art to which this disclosure pertains.

What is claimed is:

1. A simulated moving bed chromatography device comprising:
   a minimum of one stationary pipe with a plurality of inlet/outlet channels;
   a rotary device connected to the stationary pipe(s), wherein the rotary device comprises a plurality of rotational flow distribution channels employed to individually received/transfer fluid(s) from/to the inlet/outlet channels;
   a stationary segmented vessel that communicates with the rotary device, wherein the stationary segmented vessel comprises a plurality of stationary flow distribution segments, a plurality of stationary phase segments and a plurality of outer fluid transfer segments, wherein the radial direction first partition plates are set up between the adjacent stationary flow distribution segments, between the adjacent stationary phase segments, between the outer fluid transfer segments;
   a fluid moving device to circulate the fluid;
   a driver to rotate the rotary device for a fixed angle, wherein the one end of the rotational flow distribution channel of the rotary device communicates with the corresponding stationary inlet/outlet channel, the other end communicates with the next corresponding stationary flow distribution segment of the stationary segmented vessel;
   a first circulation mechanism within the stationary segmented vessel, which refers to: the first passage channels of the first partition plates in the outer fluid transfer segments and the first passage channels is:
   a plurality of openings or channels on the first partition plate within the outer fluid transfer segments, or
   a plurality of bypass channels for the first partition plate of the outer fluid transfer segments, or
   a flow channel formed by the removal of the first partition plate between the two adjacent outer fluid transfer segments.

2. The simulated moving bed chromatography device according to claim 1, wherein the rotational flow distribution channels comprises rotating flow channels and face plate openings.

3. The simulated moving bed chromatography device according to claim 2, wherein a group of two rotating flow channels including channels for importing feed and exporting raffinate is separated from the rotating flow channel for exporting extract and the rotating flow channels of the said group and the rotating flow channel for the extract are located at the opposite side of the stationary segmented vessel.

4. The simulated moving bed chromatography device according to claim 2, wherein the rotational flow distribution channels further comprises:
   a rotational flow distribution box, wherein the rotational flow distribution box is separated by the second partition plates into flow distribution compartment and each flow distribution compartment communicates with no more than one rotating flow channel through the end opening of the rotating flow channel; or,
   a plurality of L shape channels connected to the rotating flow channels.

5. The simulated moving bed chromatography device according to claim 4, wherein there is a third circulation mechanism within the rotational flow distribution box and the third circulation mechanism refers to: the third passage channels of the second partition plates in the rotational flow distribution box and the third passage channels is:
   a plurality of openings or channels on the second partition plates within the rotational flow distribution box; or
   a plurality of bypass channels for the second partition plates of the rotational flow distribution box compartments and the bypass channels for the second partition plate of the rotational flow distribution box compartments is the piping or tubing connecting the two adjacent flow distribution box compartments; or
   a flow channel formed by the removal of the second partition plate between the two adjacent rotating flow distribution compartments; or
   the flow path channels through the rotational flow distribution box compartment, rotating flow channels, stationary outlet channels, connecting pipes, stationary inlet channels, rotational flow distribution channels and the adjacent rotational flow distribution box compartment or the flow path channels through the rotational flow distribution box compartment, rotating flow channels, stationary outlet channels, fluid moving device, stationary inlet channels, rotating flow channels and the adjacent rotational flow distribution box compartment.

6. The simulated moving bed chromatography device according to claim 5, wherein the flow distribution box is separated into flow distribution compartment by the second partition plates and each said compartment is in one to one correspondence to the stationary flow distribution segment.

7. The simulated moving bed chromatography device according to claim 5, wherein for every other second partition plate in the rotational flow distribution box compartments, there is one second partition plate with third passage channel.

8. The simulated moving bed chromatography device according to claim 1, wherein the stationary phase segment has inner porous element located at the outside of the corresponding flow distribution segment between the stationary phase segment and the flow distribution segment to communicate the two segments, furthermore, the said stationary phase segment has outer porous element located at the outside of the stationary phase segment between the stationary phase segment and outer fluid transfer segment to communicate the stationary phase segment and the corresponding fluid transfer segment.

9. The simulated moving bed chromatography device according to claim 1, wherein the rotational flow distribution channel is connected to the corresponding stationary flow distribution segment and each stationary flow distribution segment is connected to no more than one rotational flow distribution channel, wherein each stationary flow distribution segment and stationary phase segment is in one to one correspondence and connected to each other and each stationary phase segment and outer fluid transfer segment is in one to one correspondence and connected to each other.

10. The simulated moving bed chromatography device according to claim 1, wherein for every other first partition plate in the outer fluid transfer segments, there is one first partition plate with first passage channel.

11. The simulated moving bed chromatography device according to claim 1, wherein the aforementioned bypass channels of the first partition plate of the outer fluid transfer segments is the piping/tubing system connected to the two adjacent outer fluid transfer segments or is the pipe/tubing system with or without a fluid moving device connected to a set of nozzle located on the two side of the first partition plate on the outer wall of the outer fluid transfer segments.

12. The simulated moving bed chromatography device according to claim 1, wherein there is a second circulation mechanism within the stationary segmented vessel and the second circulation mechanism refers to: the second passage channels of the first partition plates in the stationary flow distribution segments and the second passage channels is:
- a plurality of openings or channels on the first partition plate within the stationary flow distribution segments; or
- a plurality of bypass channels for the first partition plate of the stationary flow distribution segments and the bypass channels for the first partition plate of the stationary flow distribution segments is the piping or tubing connecting the two adjacent stationary flow distribution segments; or
- a flow channel formed by the removal of the first partition plate between the two adjacent stationary flow distribution segments.

13. The simulated moving bed chromatography device according to claim 1, wherein for every other first partition plate in the stationary flow distribution segments, there is one first partition plate with second passage channel.

14. The simulated moving bed chromatography device according to claim 1, wherein the fluid moving device is connected to a set of two adjacent nozzles located at the outer wall of two adjacent outer fluid transfer segments in the stationary segmented vessel or the fluid moving device is connected to a set of adjacent flow distribution compartments in the rotational flow distribution box through the stationary inlet/outlet pipes.

15. The simulated moving bed chromatography device according to claim 1, there are even number of the stationary phase segments.

16. The simulated moving bed chromatography device according to claim 1, wherein the rotary device rotates a fixed angle for each rotational step and the number of the rotational steps for a full 360 degree rotation either equals the number of the stationary flow distribution segment or equals to one half of the number of the stationary flow distribution segments.

17. The simulated moving bed chromatography device according to claim 1, wherein the height of the packing or filler in the stationary phase segments is higher than the heights of the opening of the inner or outer porous elements.

18. The simulated moving bed chromatography device according to claim 1, wherein there are sealing elements between the rotary device and the stationary inlet/outlet pipe and sealing elements between the rotary device and the stationary segmented vessel.

19. The simulated moving bed chromatography device according to claim 4, wherein there is a depressurization and contamination prevention system located at the outside of the rotational flow distribution box and this depressurization and contamination prevention system comprises seal leakage valve and seal leakage meter, furthermore, the seal leakage valve has inlet end communicates with the space between the innermost plate and rotational flow distribution box.

20. The simulated moving bed chromatography device according to claim 1, wherein the stationary flow distribution segments, the stationary phase segments and the outer fluid transfer segments are angularly divided equally by the first partition plates.

* * * * *